United States Patent [19]

Vincent et al.

[11] Patent Number: 4,526,755
[45] Date of Patent: Jul. 2, 1985

[54] GAS ANALYZER OR THE LIKE

[75] Inventors: Arthur L Vincent, Monrovia; James R. Robinson, Phelan; Ernst R. Ginkel, San Dimas, all of Calif.

[73] Assignee: International Telephone & Telegraph Corporation, New York, N.Y.

[21] Appl. No.: 351,238

[22] Filed: Feb. 22, 1982

[51] Int. Cl.³ .................................................. G01N 27/04
[52] U.S. Cl. ..................................... 422/90; 204/405; 422/76; 422/93; 436/114; 436/115; 436/119; 436/120; 436/123; 436/163; 436/175
[58] Field of Search ............................ 422/62, 75–77, 422/43, 90; 436/55, 114, 115, 119–123, 163, 175, 178; 204/405

[56] References Cited

U.S. PATENT DOCUMENTS

| | | | |
|---|---|---|---|
| 3,514,262 | 5/1970 | Ayers et al. | 422/93 |
| 3,692,492 | 9/1972 | Poli, Jr. et al. | 422/93 |
| 3,854,884 | 12/1974 | Robison | 422/77 |
| 3,967,933 | 7/1976 | Etess et al. | 436/118 |
| 4,325,911 | 4/1982 | Vincent | 422/75 |

Primary Examiner—Michael S. Marcus
Attorney, Agent, or Firm—T. L. Peterson; E. C. Jason

[57] ABSTRACT

An analyzer for natural gas to determine the existence of and concentration of wanted and unwanted sulfur compounds and odorizing agents.

5 Claims, 2 Drawing Figures

GAS ANALYZER OR THE LIKE

BACKGROUND OF THE INVENTION

This invention relates to gas measurement, and more particularly to a natural gas or other sulfur analyzer.

PRIOR ART STATEMENT

Coulometric titrators are known in the prior art as well as subtraction methods for concentration detection. For example, see J. R. Robison 2, U.S. Pat. No. 3,854,884, issued December 17, 1974, and J. R. Robison 3, U.S. Pat. No. 3,945,904, issued Mar. 23, 1976. In Robison 2 see also the analog subtractor in FIG. 2 and the legends at the inputs thereof.

It has been known in the prior art that a 1.0 percent solution of $CdSO_4$ with a 2.0 percent solution of $H_3BO_3$ in a scrubber will remove $H_2S$ from natural gas selectively.

It has been known in the prior art that $H_2S$ and mercaptans (RSH) can be removed from natural gas by a 10.0 percent solution of NaOH in a scrubber.

It has been known that sulfides (RSR), $H_2S$ and RSH can be removed from natural gas by a scrubber having a 0.5 percent solution of $AgNO_3$ therein.

It has been known in the prior that a device can be switched from track to hold for bias, and vice versa, upon the alternate injection of a calibration gas and a gas of interest. Such devices are, in some cases, made and sold by XEBEC Co., Ltd., No. 21-12, Kasuya 4-chome, Setagaya-ku, Tokyo, 157 Japan, as Analog Memory XE Modules. See also Jodan Technology, P.O. Box 362, Lexington, MA 02173.

In the past, a sulfur analyzer of a number of channels has not been available.

SUMMARY OF THE PRESENT INVENTION

In accordance with the analyzer of the present invention, the above-described and other disadvantages of the prior art are overcome by providing scrubbers of different kinds delivering gases in different combinations to electrical measurement apparatus from which corresponding signals are subtracted.

BRIEF DESCRIPTION OF THE DRAWINGS

In the accompanying drawings which illustrate exemplary embodiments of the present invention.

DESCRIPTION OF THE PREFERRED EMBODIMENT

Figure 1:
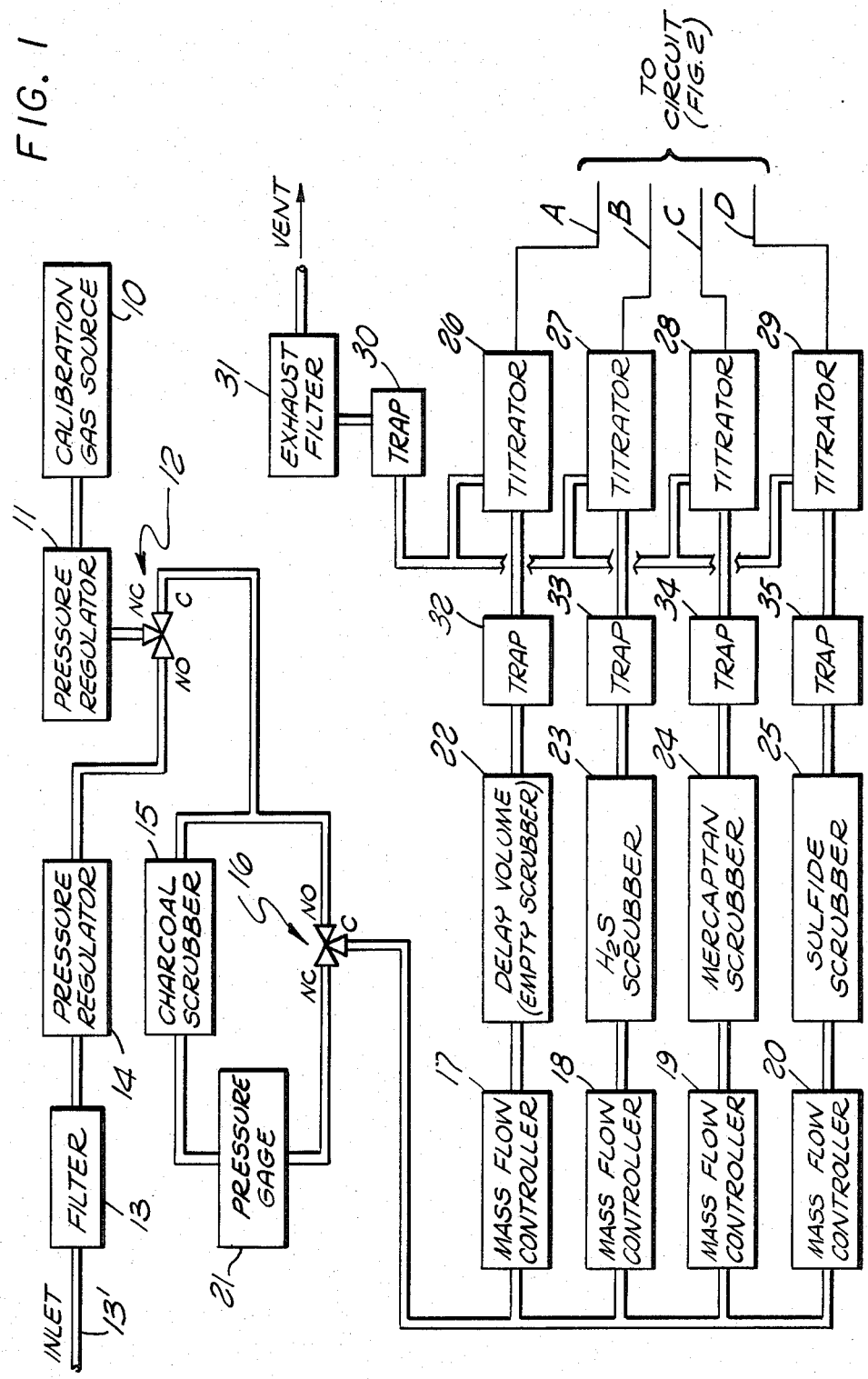
FIG. 1 is a block diagram constructed in accordance with the present invention.

In FIG. 1 a calibration gas emanates from a conventional source 10 and passes through a conventional pressure regulator 11 to a conventional valve 12.

Valve 12 also receives a gas of interest (inlet gas through conduit 13') via a conventional porous metal filter 13 and a conventional pressure regulator 14.

Valve 12 may be a conventional solenoid valve. Valve 12 first admits calibration gas to a conventional charcoal scrubber 15 and a conventional valve 16, and then admits inlet gas thereto.

Calibration gas then enters all of four conventional mass flow controllers 17, 18, 19 and 20 at the same time. When inlet gas passes to controllers 17-20, it first passes through scrubber 15 and pressure gage 21.

Controllers 17-20 admit the same rate of mass flow into each of four scrubbers 22, 23, 24 and 25, respectively. Scrubber 22 is empty and merely provides a delay volume.

Scrubber 23 contains conventional solutions of 1.0% $CdSO_4$ and 2.0% of $H_3BO_3$.

Scrubber 24 contains a conventional solution of 10.0% NaOH.

Scrubber 25 contains a conventional 0.5% solution of $AgNO_3$.

The structure of the scrubbers 22-25 may all be the same. They also may all be conventional.

Conventional coulometric titrators 26, 27, 28 and 29 are provided with respective output leads that carry electrical signals of amplitudes A, B, C and D. See these reference characters both in FIG. 1 and in FIG. 2.

Gases bubbled through titrators 26-29 are vented through a conventional moisture trap 30 and a conventional soda lime exhaust filter 31.

Conventional moisture traps 32, 33, 34 and 35 are connected respectively from scrubbers 22-25 and to titrators 26-29.

Conventional amplifiers are provided at 36, 37, 38, 39, 40, 41, 42, 43, 44 and 45. Amplifier 44 is a differential amplifier which, with resistors 46, 47, 48 and 49, is wired to be a conventional analog adder. Conventional recorders are provided at 50, 51, 52, 53 and 54.

Differential amplifiers are provided at 55, 56, 57, 58, 59, 60, 61 and 62.

A conventional sample and hold circuit of the type described hereinbefore is shown at 63, 64, 65 and 66.

Amplifiers 36-39 have respective input signals of amplitudes A-D. The outputs of amplifiers 36-39 are respectively connected to the noninverting inputs of amplifiers 55-58, respectively. The outputs of amplifiers 36-39 are also connected to the inputs of circuits 63-66. The outputs of circuits 63-66 are connected to the inverting inputs of amplifiers 55-58.

Resistors at 67, 68, 69, 70, 71, 72, 73 and 74 with their connections cause amplifiers 59-62 to produce output signals of amplitudes directly proportional to (A-B), (B-C), (C-D) and D, respectively, but with A, B, C and D provided by a constant bias by circuits 63-66.

Recorder 50 indicates total $H_2S$.

Recorder 51 indicates total RSH (mercaptans).

Recorder 52 indicates total RSR (sulfides).

Recorder 53 indicates total RSSR (organic disulfides).

Recorder 54 indicates the sum of the totals indicated on recorders 50 and 53, inclusive.

Figure 2:
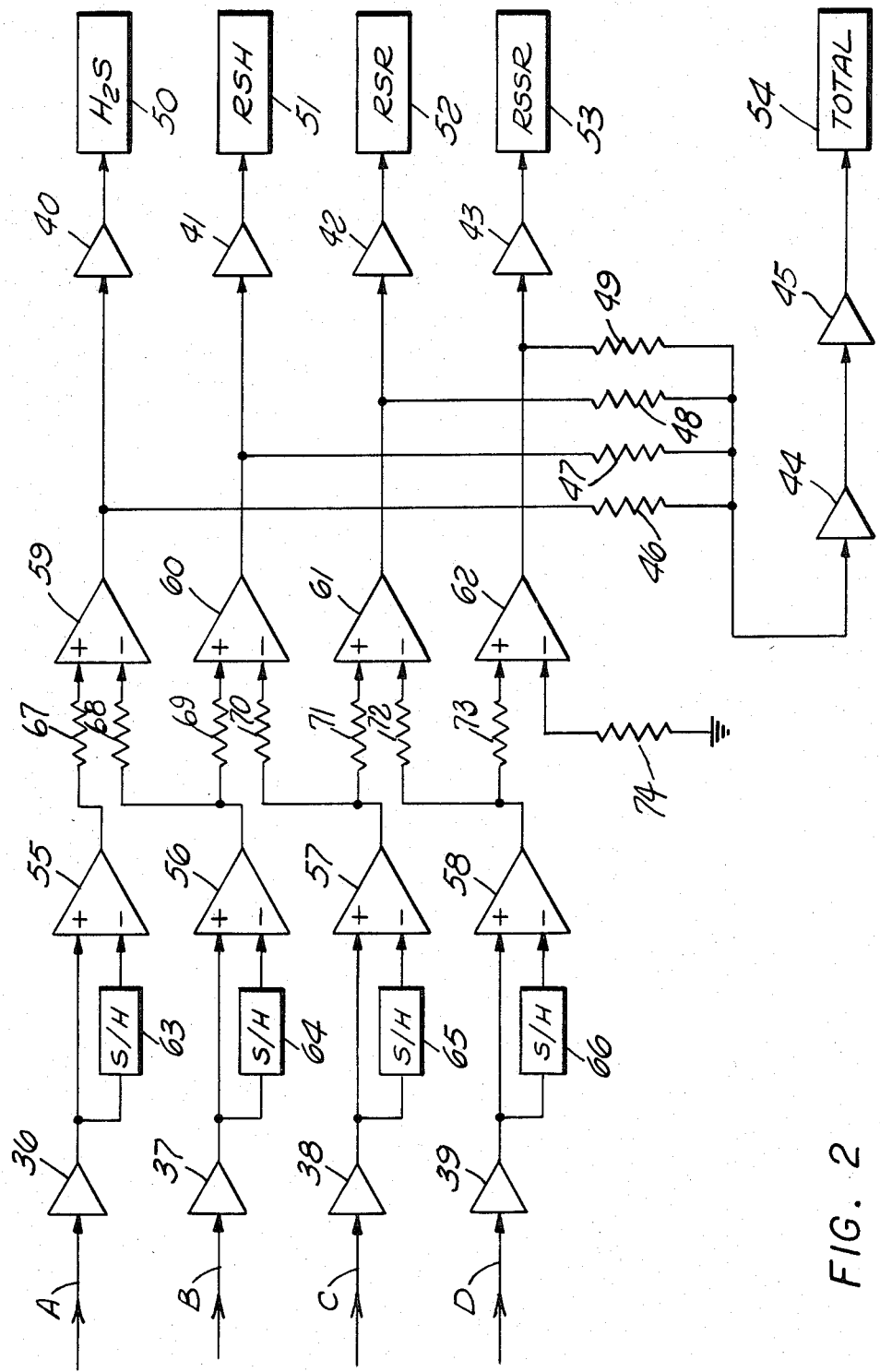
FIG. 2 is an electrical schematic constructed in accordance with the invention.

Each component shown in FIG. 1 and each component shown in FIG. 2 is, by itself, conventional. However, the same is not true of the combinations.

Excluding the biases of circuits 63-66, in general,

A ~ total sulfur (T)
B ~ T less $H_2S$
C ~ T less $H_2S$ less RSH
D ~ T less $H_2S$ less RSH less RSR Thus, $$\begin{array}{r} A \sim T \\ -B \sim -T + H_2S \\ \hline (A - B) \sim H_2S \end{array}$$

-continued
$$B \sim T - H_2S$$
$$\frac{-C \sim -T + H_2S + RSH}{(B - C) \sim RSH}$$

$$C \sim T - H_2S - RSH$$
$$\frac{-D \sim -T + H_2S + RSH + RSR}{(C - D) \sim RSR}$$

After the passage of some time, when the calibration gas is circulated, circuits 63-66 sample and hold the outputs of amplifiers 36-39 to impress thereafter a constant voltage of the sampled amplitude on the inverting inputs to amplifiers 55-58.

It is advantageous to monitor $H_2S$, RSH, RSR, RSSR and the sum of all four to detect quality, excessive odorification and undesirable properties of compounds in natural gas that is being purchased, for example.

In FIG. 1, each of the coulometric titrators 26-29 may be conventional. For example, each may be of the type disclosed in M. L. Robinson 5, U.S. Pat. No. 3,448,031, issued June 3, 1969.

We claim:

1. A gas analyzer comprising: a source of a gas of interest; at least first and second scrubbers each having an inlet and an outlet, said first scrubber providing only a delay volume equal to that of said second scrubber, said second scrubber removing at least one compound from said gas of interest; first and second coulometric titrators connected from the outputs of said first and second scrubbers, respectively, to produce first and second electrical output signals of respective amplitudes A and B directly proportional to the total sulfur concentration in said gas, including said one sulfur compound, and said concentration minus that of said one compound, respectively; means to produce a signal of a magnitude E directly proportional to (A-B), said gas source being connected to said scrubber inlets, said signal amplitude E being directly proportional to the concentration of said one compound in said gas of interest.

2. The invention according to claim 1, wherein first and second means are provided to produce respective output signals of amplitudes directly proportional to A and B, respectively, third means being provided to inject selectively a calibration gas and said gas of interest into said scrubber inlets.

3. A multichannel sulfur analyzer comprising: a source of a gas of interest; first, second, third and fourth scrubbers for removing nothing, second, third and fourth sulfur compounds, respectively, each of said scrubbers having an inlet and an outlet; first means to supply a gas of interest to all four of said scrubber inlets; first, second, third and fourth coulometric titrators connected from the outlets of the respective first, second, third and fourth scrubbers to produce electrical output signals of magnitudes A, B, C and D, respectively, where A is directly proportional to total sulfur content of said gas of interest in compounds $H_2S$, RSH and RSSR, B is directly proportional to said total content minus the $H_2S$ content, C is directly proportional to said total content minus said $H_2S$ content minus the RSH content, and D is said total content minus said $H_2S$ content, minus said RSH content, minus said RSR content; second means to produce an output signal directly proportional to E, where E=A-B and E is directly proportional to the said $H_2S$ content; third means to produce an output signal directly proportional to F, where F=B-C and F is directly proportional to said RSH content; and fourth means to produce an output signal directly proportional to G, where G=C-D and G is directly proportional to said RSR content.

4. The invention according to claim 3, wherein a calibration gas source is provided, a valve to switch said scrubber inlets from said calibration gas source to said first means, a first set of differential amplifiers connected to receive signals of respective amplitudes proportional to A, B, C and D on corresponding inputs thereof, and fifth means responsive to flow of said calibration gas for setting a calibrating bias on respective non-corresponding inputs of said differential amplifiers.

5. The invention according to claim 4, wherein sixth means are provided to produce an electrical output signal H where H is directly proportional to the sum (E+F+G+D).

* * * * *